United States Patent
Kubota et al.

(10) Patent No.: US 10,998,574 B2
(45) Date of Patent: May 4, 2021

(54) NON-AQUEOUS ELECTROLYTE MAGNESIUM SECONDARY BATTERY

(71) Applicant: NATIONAL INSTITUTE OF ADVANCED INDUSTRIAL SCIENCE AND TECHNOLOGY, Tokyo (JP)

(72) Inventors: Keigo Kubota, Osaka (JP); Kenichi Teramoto, Osaka (JP); Rie Ooyabu, Osaka (JP); Hajime Matsumoto, Osaka (JP)

(73) Assignee: NATIONAL INSTITUTE OF ADVANCED INDUSTRIAL SCIENCE AND TECHNOLOGY, Tokyo (JP)

( * ) Notice: Subject to any disclaimer, the term of this patent is extended or adjusted under 35 U.S.C. 154(b) by 340 days.

(21) Appl. No.: 15/517,349

(22) PCT Filed: Oct. 8, 2015

(86) PCT No.: PCT/JP2015/078651
§ 371 (c)(1),
(2) Date: Apr. 6, 2017

(87) PCT Pub. No.: WO2016/056629
PCT Pub. Date: Apr. 14, 2016

(65) Prior Publication Data
US 2017/0294675 A1    Oct. 12, 2017

(30) Foreign Application Priority Data

Oct. 8, 2014    (JP) .............................. JP2014-207313

(51) Int. Cl.
*H01M 10/054* (2010.01)
*H01M 10/056* (2010.01)
(Continued)

(52) U.S. Cl.
CPC ......... *H01M 10/054* (2013.01); *C07C 211/63* (2013.01); *C07C 309/06* (2013.01);
(Continued)

(58) Field of Classification Search
CPC ..... H01M 4/466; H01M 10/054; H01M 10/05
See application file for complete search history.

(56) References Cited

U.S. PATENT DOCUMENTS

| | | |
|---|---|---|
| 2004/0137324 A1 | 7/2004 | Itaya et al. |
| 2007/0092803 A1 | 4/2007 | Nakanishi et al. |

(Continued)

FOREIGN PATENT DOCUMENTS

| | | |
|---|---|---|
| CN | 102047491 | 5/2011 |
| JP | 2004-327326 | 11/2004 |

(Continued)

OTHER PUBLICATIONS

Pereira-Ramos et al., "Electrochemical Formation of a Magnesium Vanadium Bronze $Mg_xV_2O_5$ in Sulfone-based Electrolytes at 150° C.", Journal of Electroanal Chem, 218: 241-249 (1987).
(Continued)

*Primary Examiner* — James Lee
(74) *Attorney, Agent, or Firm* — Wenderoth, Lind & Ponack, L.L.P.

(57) ABSTRACT

This invention provides a non-aqueous electrolyte magnesium secondary battery comprising a positive electrode, a negative electrode, a separator, and a non-aqueous electrolyte, the non-aqueous electrolyte comprising $[N(SO_2CF_3)_2]^-$ as an anion, and $Mg^{2+}$ and/or an organic onium cation as a cation.

6 Claims, 8 Drawing Sheets

(51) Int. Cl.
  *H01M 10/0568* (2010.01)
  *H01M 10/0569* (2010.01)
  *H01M 4/38* (2006.01)
  *H01M 4/48* (2010.01)
  *C07C 211/63* (2006.01)
  *C07C 309/06* (2006.01)
  *C07C 309/21* (2006.01)
  *C07F 9/54* (2006.01)
  *H01M 4/46* (2006.01)

(52) U.S. Cl.
  CPC .......... *C07C 309/21* (2013.01); *C07F 9/5407* (2013.01); *H01M 4/381* (2013.01); *H01M 4/466* (2013.01); *H01M 4/483* (2013.01); *H01M 10/056* (2013.01); *H01M 10/0568* (2013.01); *H01M 10/0569* (2013.01); *H01M 2300/0045* (2013.01)

(56) References Cited

U.S. PATENT DOCUMENTS

| | | | |
|---|---|---|---|
| 2010/0136438 A1* | 6/2010 | Nakayama | H01M 10/054 429/339 |
| 2011/0111286 A1 | 5/2011 | Yamamoto et al. | |
| 2014/0170507 A1 | 6/2014 | Matsui et al. | |
| 2014/0242473 A1 | 8/2014 | Hirashita et al. | |
| 2015/0050565 A1* | 2/2015 | Lamanna | H01M 4/13 429/339 |
| 2015/0255830 A1 | 9/2015 | Matsui et al. | |
| 2016/0156063 A1* | 6/2016 | Mizuno | H01M 4/381 429/80 |

FOREIGN PATENT DOCUMENTS

| | | |
|---|---|---|
| JP | 2014-167871 | 9/2014 |
| WO | 2013/122783 | 8/2013 |
| WO | 2013/157187 | 10/2013 |
| WO | 2015/029291 | 3/2015 |

OTHER PUBLICATIONS

Vardar et al., "Electrochemistry of Magnesium Electrolytes in Ionic Liquids for Secondary Batteries", ACS Applied Materials & Interfaces, 6: 18033-18039 (2014).
International Search Report, dated Dec. 28, 2015 in corresponding International Application No. PCT/JP2015/078651.
Partial Supplementary European Search Report dated Apr. 16, 2018 in European Application No. 15848695.1.
Extended European Search Report dated Jul. 11, 2018 in European Application No. 15848695.1.
Office Action dated Jul. 3, 2019 in corresponding Chinese Patent Application No. 201580051614.5, with English translation.

* cited by examiner

① Electrolyte-impregnated separator
② Negative electrode
③ Composite electrode material
④ Stainless-steel container
⑤ Insulation packing

NON-AQUEOUS ELECTROLYTE MAGNESIUM SECONDARY BATTERY

TECHNICAL FIELD

The present invention relates to a non-aqueous electrolyte magnesium secondary battery.

BACKGROUND ART

Magnesium secondary batteries, which have a high theoretical capacity density and abundant resources, and which are highly safe, are expected to find practical application as batteries that are more excellent than lithium secondary batteries. Compared with monovalent lithium ions, however, divalent magnesium ions have a strong interaction, and are unlikely to diffuse in solid phase.

Non-patent Literature 1 reports electrochemical insertion of $Mg^{2+}$ into $V_2O_5$, but is silent about a magnesium secondary battery.

Non-patent Literature 2 only discloses Mg metal electrolytic deposition/remelting behavior in an ionic liquid, and no battery data are shown.

CITATION LIST

Non-Patent Literature

NPL 1: J. P. Pereira-Ramos, R. Messna, J. Perichon, J. Electroanal. Chem, 218, 241 (1987).

NPL 2: Gulin Vardar, Alice Sleightholme, Junichi Naruse, Hidehiko Hiramatsu, Donald J. Siegel, and Charles W., Electrochemistry of Magnesium Electrolytes in Ionic Liquids for Secondary Batteries, Monroe ACS Appl. Mater. Interfaces, Publication Date: (Web) 23 Sep. 2014.

SUMMARY OF INVENTION

Technical Problem

An object of the present invention is to provide a non-aqueous electrolyte magnesium secondary battery that is safe and has a practically applicable charge-and-discharge capacity.

Solution to Problem

The present invention provides the following non-aqueous electrolyte magnesium secondary battery.

Item 1. A non-aqueous electrolyte magnesium secondary battery comprising a positive electrode, a negative electrode, a separator, and a non-aqueous electrolyte, the non-aqueous electrolyte comprising $[N(SO_2CF_3)_2]^-$ as an anion, and $Mg^{2+}$ and/or an organic onium cation as a cation.

Item 2. The non-aqueous electrolyte magnesium secondary battery according to Item 1, wherein the negative electrode comprises a negative electrode active material selected from the group consisting of a metal magnesium, magnesium alloy materials, carbon materials, and composite materials of metal magnesium or a magnesium alloy with a carbon material.

Item 3. The non-aqueous electrolyte magnesium secondary battery according to Item 1, wherein the positive electrode comprises a positive active material, the positive active material being a material in which magnesium ions undergo an insertion/extraction reaction.

Item 4. The non-aqueous electrolyte magnesium secondary battery according to Item 3, wherein the material in which magnesium ions undergo an insertion/extraction reaction is at least one member selected from the group consisting of metal sulfides free from magnesium, metal oxides free from magnesium, oxides obtained by removing Li from Li-containing composite oxides and replacing the Li with an Mg ion, Chevrel materials, polyanion materials, silicate materials, magnesium nitride, organic positive-electrode materials, compounds comprising a transition metal and fluorine, and halogenated compounds as a positive-electrode material.

Item 5. The non-aqueous electrolyte magnesium secondary battery according to Item 3, wherein the material in which magnesium ions undergo an insertion/extraction reaction is at least one member selected from the group consisting of $TiS_2$, $MoS_2$, $NbSe_2$, $CoS$, $V_2O_5$, $V_8O_{13}$, $MnO_2$, $CoO_2$, $MgMn_2O_4$, $MgNi_2O_4$, $MgCo_2O_4$, $MgAlO_3$, $MgMnO_2$, $MgFeO_3$ $MgFe_{0.5}Mn_{0.5}O_3$, $MgFe_{0.9}Al_{0.1}O_2$, $MgMn_{0.9}Al_{0.1}O_2$, $Mg_{0.5}Mn_{0.9}Al_{0.1}O_2$, $Mo_6S_8$, $MxMo_6S_8$ (M=Cu, Ni, Ag, a transition metal, 0≤x≤2), $Cu_{0.13}Mg_{1.09-1.12}Mo_6S_8$, $MgHf(MoO_4)_3$, $Mg_{0.5}Hf_{0.5}Sc_{1.0}(MoO_4)_3$, $Mg_{0.2}Zr_{0.2}Sc_{1.6}(WO_4)_3$, $Mg_{0.4}Zr_{0.4}Sc_{1.2}(WO_4)_3$, $Mg_{0.6}Zr_{0.6}Sc_{1.2}(WO_4)_3$, $Mg_{0.8}Zr_{0.8}Sc_{0.4}(WO_4)_3$, $MgZr(WO_4)_3$, $MgCoSiO_4$, $MgFeSiO_4$, $MgNiSiO_4$, $Mg(Ni_{0.9}Mn_{0.1})SiO_4$, $MgFe_{0.9}Si_{0.1}O_3$, $MgFe_{0.5}Si_{0.5}O_3$, $MgFe_{0.1}Si_{0.9}O_3$, $Mg_{1.023}(Mn_{0.956}V_{0.014})SiO_4$, $FeF_{2.8}Cl_{0.2}MgCOSiO_4$, $MgMn_{0.9}Si_{0.1}O_3$, $Mg_{0.9925}(Co_{0.985}V_{0.015})SiO_4$, $Mg_{0.959}(Fe_{0.918}V_{0.082})SiO_4$, $Mg_{0.95}(Ni_{0.9}V_{0.100})SiO_4$, magnesium nitride, magnesium porphyrin, polythiophenes, $FeF_3$, and $MnF_3$.

Item 6. The non-aqueous electrolyte magnesium secondary battery according to any one of Items 1 to 5, wherein the organic onium cation has a symmetrical structure.

Item 7. The non-aqueous electrolyte magnesium secondary battery according to any one of Items 1 to 5, wherein the organic onium cation is ammonium, and the difference in the carbon numbers of four groups attaching to the nitrogen of the ammonium is 1 or 0.

Item 8. The non-aqueous electrolyte magnesium secondary battery according to any one of Items 1 to 5, wherein the organic onium cation is represented by Formula (II) below:

(II)

wherein X represents N or P, all Rs are identical, and each represents $C_{1-10}$ straight or branched alkyl, or adjacent two Rs, taken together with X, form a 3- to 11-membered heterocyclic group.

Item 9. The non-aqueous electrolyte magnesium secondary battery according to any one of Items 1 to 5, wherein the organic onium cation is represented by Formula (III) below:

(III)

wherein X represents N or P, all Rs are identical, and each represents $C_{1-10}$ straight or branched alkyl.

Item 10. The non-aqueous electrolyte magnesium secondary battery according to any one of Items 1 to 5, wherein the organic onium cation is at least one member selected from the group consisting of tetramethylammonium ($N_{1111}$), tetraethylammonium ($N_{2222}$), tetra n-propylammonium ($N_{3333}$), tetra n-butylammonium ($N_{4444}$), tetra n-pentylammonium ($N_{5555}$) 5-azoniaspiro[4.4]nonane ($AS_{44}$), tetraethylphosphonium ($P_{2222}$), and 5-phosphonia-spiro[4.4]nonane ($PS_{44}$).

Item 11. The non-aqueous electrolyte magnesium secondary battery according to Item 10, wherein the organic onium cation is tetraethylammonium ($N_{2222}$) or 5-azoniaspiro[4.4]nonane ($AS_{44}$).

Advantageous Effects of Invention

According to the present invention, a non-aqueous electrolyte magnesium secondary battery is obtained that is capable of being charged and discharged to near theoretical capacity multiple times. In particular, tetraethylammonium ($N_{2222}$), which can be charged and discharged to the theoretical capacity even when charge and discharge are repeated, and has high charge/discharge capacity retention, is preferable.

DESCRIPTION OF EMBODIMENTS

Figure 1:
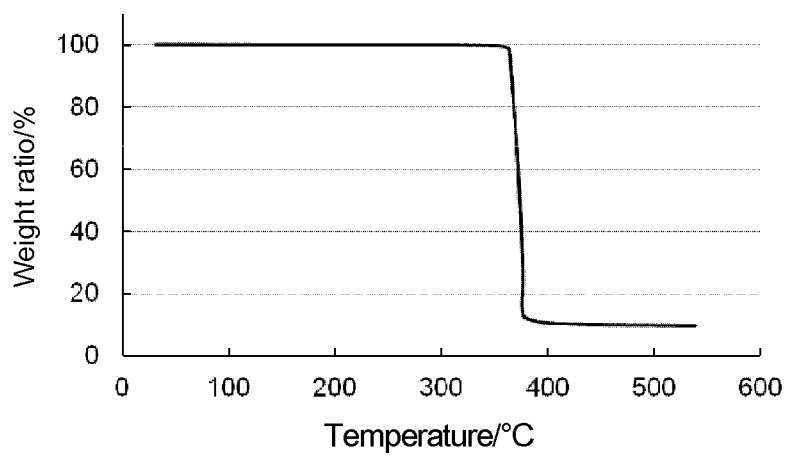
FIG. 1: Thermogravimetric analysis of $Mg[Tf_2N]_2$. Thermogravimetric analysis of $Mg[Tf_2N]_2$ was performed under a nitrogen gas flow at a temperature elevation rate of $10°$ $C.·min^{-1}$.

As the negative electrode of the magnesium secondary battery of the present invention, it is possible to use metal magnesium, and as a negative electrode active material, it is possible to use magnesium alloy materials (e.g., Mg—In alloy, Mg—Zn alloy, Mg—Sn alloy, Mg—Cd alloy, Mg—Co alloy, Mg—Mn alloy, Mg—Ga alloy, Mg—Pb alloy, Mg—Ni alloy, Mg—Cu alloy, Mg—Al alloy, Mg—Ca alloy, Mg—Li alloy, Mg—Al—Zn alloy, and Mg—In—Ni), carbon materials (e.g., graphite, carbon fiber, amorphous carbon, and graphene), composite materials of metal magnesium or a magnesium alloy with a carbon material (e.g., magnesium alloy-graphite, metal magnesium-carbon fiber, magnesium alloy-carbon fiber, metal magnesium-amorphous carbon, and magnesium alloy-amorphous carbon), and the like.

As the positive electrode, a positive active material, such as a material in which magnesium ions undergo an insertion/ extraction reaction, is used. Specific examples include metal sulfides free from magnesium and metal oxides free from magnesium (e.g., $TiS_2$, $MoS_2$, $NbSe_2$, $CoS$, $V_2O_5$, $V_8O_{13}$, $MnO_2$, and $CoO_2$), oxides obtained by removing Li from Li-containing composite oxides and replacing the Li with an Mg ion (e.g., $MgMn_2O_4$, $MgNi_2O_4$, $MgCo_2O_4$, $MgAlO_3$, $MgMnO_3$, $MgFeO_3MgFe_{0.5}Mn_{0.5}O_3$, $MgFe_{0.9}Al_{0.1}O_3$, $MgMn_{0.9}Al_{0.1}O_3$, $Mg_{0.5}Mn_{0.9}Al_{0.1}O_2$), Chevrel materials ($Mo_6S_8$, $MxMo_6S_8$ (M=Cu, Ni, Ag, transition metal, $0 \le x \le 2$), $Cu_{0.13}Mg_{1.09-1.12}Mo_6S_8$), polyanion materials ($MgHf(MoO_4)_3$, $Mg_{0.5}Hf_{0.5}Sc_{1.0}(MoO_4)_3$, $Mg_{0.2}Zr_{0.2}Sc_{1.6}(WO_4)_3$, $Mg_{0.4}Zr_{0.4}Sc_{1.2}(WO_4)_3$, $Mg_{0.6}Zr_{0.6}Sc_{1.2}(WO_4)_3$, $Mg_{0.8}Zr_{0.8}Sc_{0.4}(WO_4)_3$, $MgZr(WO_4)_3$), silicate materials (e.g., $MgCoSiO_4$, $MgFeSiO_4$, $MgNiSiO_4$, $Mg(Ni_{0.9}Mn_{0.1})SiO_4$, $MgFe_{0.9}Si_{0.1}O_3$, $MgFe_{0.5}Si_{0.5}O_3$, $MgFe_{0.1}Si_{0.9}O_3$, $Mg_{1.023}(Mn_{0.956}V_{0.014})SiO_4$, $FeF_{2.8}Cl_{0.2}MgCOSiO_4$, $MgMn_{0.9}Si_{1.1}O_3$, $Mg_{0.9925}(Co_{0.985}V_{0.015})SiO_4$, $Mg_{0.959}Fe_{0.918}V_{0.082})SiO_4$, and $Mg_{0.95}(Ni_{0.9}V_{0.100})SiO_4$), magnesium nitride, organic positive-electrode materials (e.g., magnesium porphyrin, polythiophenes), compounds comprising transition metal and fluorine (e.g., $FeF_3$, $MnF_3$), halogenated compounds as a positive-electrode material, and the like. A known material in which lithium ions undergo an insertion/extraction reaction (optionally Li being replaced with Mg) in a lithium secondary battery may be used as a material in which magnesium ions undergo an insertion/extraction reaction in the non-aqueous electrolyte magnesium secondary battery of the present invention. The material in which magnesium ions undergo an insertion/extraction reaction is preferably $V_2O_5$, $MgMn_2O_4$, $MgNi_2O_4$, and $MgCo_2O_4$.

The positive electrode is obtained by forming, on a collector, a positive-electrode-active-material layer containing a positive electrode active material, a binding agent, a conductive auxiliary agent, and the like.

The negative electrode may be metal magnesium, and is obtained by forming, on a collector, a negative-electrode-active-material layer containing a negative electrode active material, a binding agent, and the like.

Examples of a binding agent used for the positive electrode and negative electrode include water-soluble polymers such as polyimide, carboxymethyl cellulose, cellulose, diacetyl cellulose, methyl cellulose, hydroxyethyl cellulose, hydroxypropyl cellulose, sodium alginate, polyacrylic acid, sodium polyacrylate, polyvinyl phenol, polyvinyl methyl ether, polyvinyl alcohol, polyvinyl pyrrolidone, polyacrylonitrile, polyacrylamide, polyhydroxy(meth)acrylate, and styrene-maleic acid copolymer;
emulsions (latexes), such as polyvinyl chloride, polytetrafluoroethylene, polyvinylidene fluoride (PVDF), tetrafluoroethylene-hexafluoropropylene copolymer, vinylidene fluoride-tetrafluoroethylene-hexafluoropropylene copolymer, polyethylene, polypropylene, ethylene-propylene-diene terpolymer (EPDM), sulfonated EPDM, polyvinyl acetal resin, (meth)acrylic acid ester-containing (meth) acrylic acid ester copolymers, such as methyl methacrylate and 2-ethylhexyl acrylate, vinyl ester-containing polyvinyl ester copolymers, such as (meth)acrylic acid ester-acrylonitrile copolymer and vinyl acetate, styrene-butadiene copolymers, acrylonitrile-butadiene copolymers, polybutadiene, neoprene rubber, fluororubber, polyethylene oxide, polyester-polyurethane resin, polyether-polyurethane resin, polycarbonate-polyurethane resin, polyester resin, phenol resin, and epoxy resin; and the like, with polyimide being preferable.

Examples of a conductive auxiliary agent include vapor-grown carbon fiber (VGCF), Ketjen black (KB), carbon black, acetylene black, polyphenylene derivatives, and the like.

As a collector, it is preferable to use metal plates, such as aluminum, stainless steel, nickel, and titanium, and the like. It is also preferable to use aluminum and stainless steel whose surface is covered with carbon, nickel, titanium, or silver, and alloys obtained by incorporating carbon, nickel, titanium, or silver into the surface of the aluminum or stainless steel.

As the coating liquid for providing a positive-electrode-active-material layer or a negative-electrode-active-material layer on a collector, for example, a slurry coating liquid may be used, optionally comprising a conductive auxiliary agent mentioned above, a positive or negative electrode active material mentioned above, a binding agent mentioned above, and a dispersion medium, such as N-methyl-2-pyrrolidone (NMP), water, and toluene.

Examples of a method for applying the coating liquid to a collector include reverse roll coating, direct roll coating, blade coating, knife coating, extrusion coating, curtain coating, gravure coating, bar coating, dip coating, and squeeze coating. Of these, blade coating, knife coating, and extrusion coating are preferable. The application is preferably performed at a rate of 0.1 to 100 m/min. The application method may be selected from the above in view of the solution properties and drying properties of the coating liquid; in this way, it is possible to obtain an excellent surface state of the coating layer. The application of the coating liquid may be performed sequentially with respect to one surface at a time, or both surfaces simultaneously.

The non-aqueous electrolyte comprises $[N(SO_2CF_3)_2]^-$ as an anion, and $Mg^{2+}$ and/or an organic onium cation as a cation. Hereinbelow, $[N(SO_2CF_3)_2]$ is abbreviated as "$[Tf_2N]$."

Examples of an organic onium cation include the following ammonium, guanidinium, phosphonium, and sulfonium cations.

(1) Ammonium cations represented by Formula (Ia):

In Formula (Ia), $R^1$, $R^2$, $R^3$, and $R^4$ are identical or different, and each represents hydrogen, alkyl, alkoxy, polyether, substituted or unsubstituted aryl, substituted or unsubstituted aralkyl, or alkoxyalkyl; and in Formula (Ia), $R^1$ and $R^2$, or $R^3$ and $R^4$, taken together with the nitrogen atom, may form a 5- to 8-membered substituted or unsubstituted nitrogen-containing heterocyclic group.

(2) Guanidinium cations represented by Formula (Ib):

In the formula, $R^1$ and $R^2$ are identical or different, and each represents hydrogen, alkyl, alkoxy, polyether, substituted or unsubstituted aryl, substituted or unsubstituted aralkyl, or alkoxyalkyl.

(3) Phosphonium cations represented by Formula (Ic):

In the formula, $R^1$, $R^2$, $R^3$, and $R^4$ are identical or different, and each represents hydrogen, alkyl, alkoxy, polyether, substituted or unsubstituted aryl, substituted or unsubstituted aralkyl, or alkoxyalkyl. In Formula (Ic), $R^1$ and $R^2$, or $R^3$ and $R^4$, taken together with the phosphorus atom, may form a 5- to 8-membered substituted or unsubstituted phosphorus-containing heterocyclic group.

(4) Sulfonium cations represented by Formula (Id):

  (Id)

In the formula, $R^1$, $R^2$, and $R^3$ are identical or different, and each represents hydrogen, alkyl, alkoxy, polyether, substituted or unsubstituted aryl, substituted or unsubstituted aralkyl, or alkoxyalkyl.

When an electrolyte is produced, a silver salt, barium salt, or calcium salt, that contains an anion represented by $[Tf_2N]^-$ is mixed with a halide salt or sulfate salt, that contains the organic onium cation mentioned above to form a insoluble salt, such as a silver halide, barium sulfate, and calcium sulfate, followed by removal.

Examples of the alkyl represented by $R^1$ to $R^4$ of organic onium cation include straight or branched alkyl having 1 to 20, preferably 1 to 10, more preferably 1 to 6, and particularly preferably 1 to 3 carbon atoms, such as methyl, ethyl, n-propyl, isopropyl, n-butyl, sec-butyl, isobutyl, t-butyl, pentyl, hexyl, heptyl, octyl, nonyl, decyl, undecyl, dodecyl, tridecyl, tetradecyl, hexadecyl, octadecyl, and eicosyl.

Examples of straight or branched alkyl having 1 to 10 carbon atoms include methyl, ethyl, n-propyl, isopropyl, n-butyl, sec-butyl, isobutyl, t-butyl, pentyl, hexyl, heptyl, octyl, nonyl, and decyl.

Examples of alkoxy include straight or branched alkoxy having 1 to 20, preferably 1 to 10, more preferably 1 to 6, and particularly preferably 1 to 3 carbon atoms, and having the structure of (O-alkyl above).

Examples of aryl include aryl having 6 to 14, and preferably 6 to 10 carbon atoms, such as phenyl, toluyl, xylyl, ethylphenyl, 1,3,5-trimethyl phenyl, naphthyl, anthranil, and phenanthryl.

Examples of aralkyl include aralkyl having 7 to 15 carbon atoms, such as benzyl, phenethyl, and naphthylmethyl.

The alkoxy and alkyl in alkoxyalkyl are the same as described above. Examples include straight or branched alkyl having 1 to 20, preferably 1 to 10, more preferably 1 to 6, and particularly preferably 1 to 3 carbon atoms, substituted with straight or branched alkoxy having 1 to 20, preferably 1 to 10, more preferably 1 to 6, and particularly preferably 1 to 3 carbon atoms. In particular, examples of alkoxyalkyl include methoxymethyl ($CH_2OCH_3$), methoxyethyl ($CH_2CH_2OCH_3$), ethoxymethyl ($CH_2OCH_2CH_3$), and ethoxyethyl ($CH_2CH_2OCH_2CH_3$).

Examples of polyether include groups represented by $-(CH_2)_{n1}-O-(CH_2CH_2O)_{n2}-(C_{1-4}$ alkyl$)$ or $-(CH_2)_{n1}-O-(CH_2CH(CH_3)O)_{n2}-(C_{1-4}$ alkyl$)$, wherein n1 is an integer of 1 to 4, n2 is an integer of 1 to 4, and examples of $C_1$-$C_4$ alkyl include methyl, ethyl, n-propyl, isopropyl, n-butyl, isobutyl, sec-butyl, and tert-butyl.

Further, $R^1$ and $R^2$, or $R^3$ and $R^4$, taken together with the nitrogen atom to which they are attached, may form a 5- to 8-membered, and preferably 5- or 6-membered, nitrogen-containing heterocyclic group, such as pyrrolidinium, piperidinium, pyrrolinium, pyridinium, and imidazolium.

The following are examples of 3- to 11-membered nitrogen-containing or phosphorus-containing heterocyclic groups formed by adjacent two R groups, taken together with X.

 $AS_{22}^+$

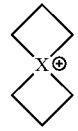 $AS_{33}^-$

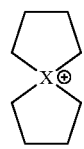 $AS_{44}^+$

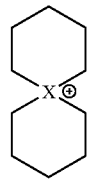 $AS_{55}^+$

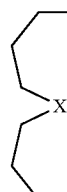 $AS_{66}^+$

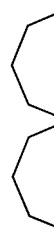 $AS_{77}^+$

X represents N or P.

The organic onium cation of Formula (II) has a symmetrical structure since four R groups are identical. Further, the organic onium cation of Formula (III), which has a methyl group and three identical R groups, has a symmetrical structure.

Examples of substituents for aryl and aralkyl include halogen (F, Cl, Br, I), hydroxyl, methyl, methoxy, nitro, acetyl, acetylamino, and the like.

One or more —O—, —COO—, and —CO— groups may be inserted at an arbitrary position or positions between the C—C single bonds in an alkyl group mentioned above to thus form an ether, ester, or ketone structure.

In a preferable embodiment of the present invention, an organic onium cation is represented by Formula (II) below.

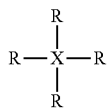
(II)

In the formula, X represents N or P; all Rs are identical, and each represents $C_{1-10}$ straight or branched alkyl, or adjacent two R groups, taken together with X, form a 3- to 11-membered heterocyclic group.

X is preferably N. R represents straight or branched alkyl having 1 to 10, preferably 1 to 6, more preferably 1 to 4, and even more preferably 1 to 3 carbon atoms. R is most preferably ethyl.

In other preferable embodiment of the present invention, the organic onium cation is represented by Formula (III) below.

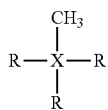
(III)

In the formula, X represents N or P; and all Rs are identical, and each represents $C_{1-10}$ straight or branched alkyl.

X preferably represents N. R represents straight or branched alkyl having 1 to 10, preferably 1 to 6, more preferably 1 to 4, and even more preferably 1 to 3 carbon atoms. R most preferably represents methyl.

The following are examples of organic onium cations.

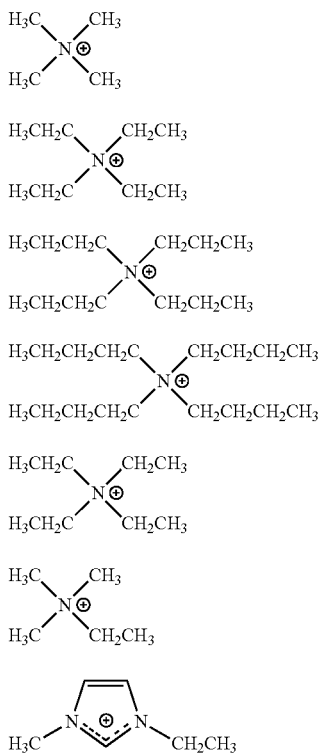

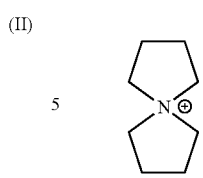
$AS_{44}{}^1$

In one embodiment, organic onium used in the present invention is preferably those having a symmetrical structure, such as AS44, AS55, $[N_{1,1,1,1}]$, $[N_{2,2,2,2}]$, $[N_{3,3,3,3}]$, $[N_{4,4,4,4}]$, $[P_{2,2,2,2}]$ $[P_{3,3,3,3}]$, and $[P_{4,4,4,4}]$, since they show excellent charge/discharge capacity retention. For example, it is sufficient if the difference in the carbon numbers of the carbon chains attaching to the nitrogen is 1 as in EMI, which has carbon numbers 1 (methyl, methylene) and 2 (ethyl, ethylene). The difference in the carbon numbers of four groups attaching to the nitrogen of ammonium is 1 or 0, and preferably 0. The difference in the carbon numbers of organic oniums $[N_{1,1,1,2}]$, $[N_{1,1,2,2}]$, $[N_{1,2,2,2}]$ $[P_{1,1,1,2}]$, $[P_{1,1,2,2}]$, and $[P_{1,2,2,2}]$ is 1. The difference in the carbon numbers of symmetrical organic oniums, such as AS44, AS55, $[N_{2,2,2,2}]$, $[N_{3,3,3,3}]$, $[N_{4,4,4,4}]$, $[P_{2,2,2,2}]$, $[P_{3,3,3,3}]$, and $[P_{4,4,4,4}]$, is 0.

Accordingly, in terms of ammonium and phosphonium, it is most preferable that the four groups attaching to the nitrogen atom or phosphorus atom are equivalent to each other, and in tams of sulfonium, it is most preferable that the three groups attaching to the sulfur atom are equivalent to each other.

The electrolyte used in the present invention may further contain other electrolytes, such as a salt of $[Tf_2N]$ with an alkali metal (e.g., Li, Na, K, and Cs).

The magnesium secondary battery of the present invention may further contain other ionic liquids.

The magnesium secondary battery of the present invention contains a separator and the like, in addition to the positive electrode, negative electrode, and electrolyte described above.

The electrolyte of the present invention is usually used by filling in or being impregnated into a separator and voids within an electrode.

Each constituent element described above is enclosed in a known various cell casing, such as a coin type, a cylinder type, and a laminate package, and sealed to obtain a magnesium secondary battery.

EXAMPLES

The present invention is described in more detail below with reference to Examples and Comparative Examples. However, the present invention is not limited to these Examples.

Reference Example 1

FIG. 1 shows the results of thermogravimetric analysis of $Mg[Tf_2N]_2$, which is an electrolyte salt. The measurement was performed in a nitrogen gas atmosphere at a temperature elevation rate of $10°$ C.·$min^{-1}$. It was clarified that an Mg salt containing $[Tf_2N]$, which is known to have high thermal resistance, was also stable until the temperature reached $300°$ C. or higher.

Example 1

Figure 2:
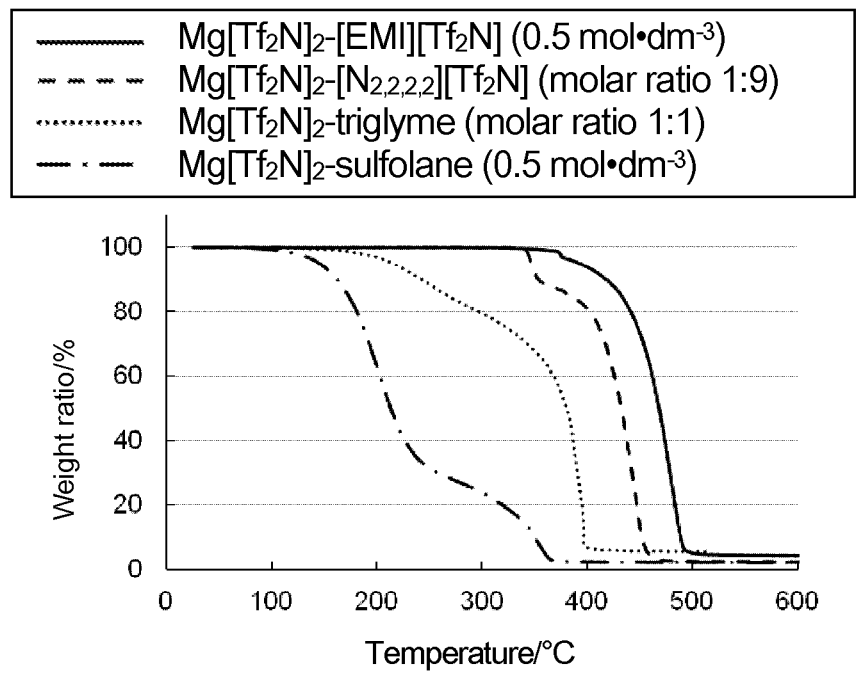
FIG. 2: Thermogravimetric analysis of an electrolyte containing $Mg[Tf_2N]_2$. A thermogravimetric analysis was performed on an electrolyte to which $Mg[Tf_2N]_2$ was added as an electrolyte salt.

FIG. 2 shows the results of thermogravimetric analysis performed for electrolyte solutions obtained by adding $Mg[Tf_2N]_2$ as an electrolyte salt to various solvents. The analysis was performed under the same conditions as in Reference Example 1. The electrolyte solutions that use organic solvents such as triglyme or sulfolane were volatilized at 200° C. or lower; however, electrolyte solutions that use solvents such as $[N_{2,2,2,2}]$ $[Tf_2N]$ or [EMI] $[Tf_2N]$, which are $[Tf_2N]$-containing ionic liquids as in $Mg[Tf_2N]_2$, were stable until the temperature reached 300° C. or higher.

Example 2

Figure 3:
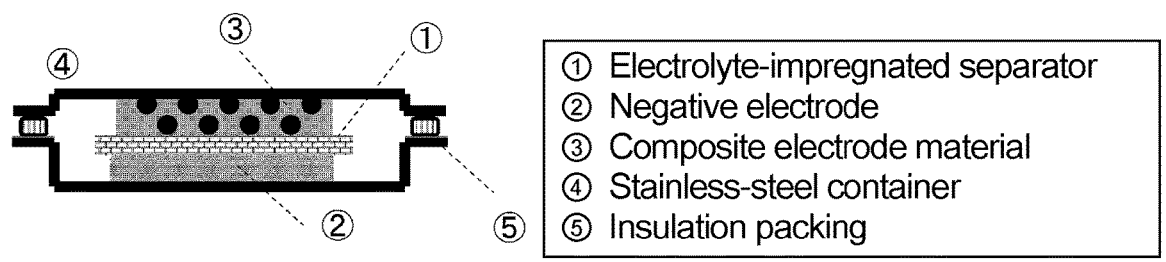
FIG. 3: A schematic diagram of a battery test cell. A bipolar electrochemical test cell was constructed by combining an electrolyte solution, a negative electrode, and a mixed positive electrode material. The assembly was performed in an argon gas atmosphere with a moisture concentration of 0.5 ppm or less and an oxygen concentration of 0.5 ppm or less.

As an Example of the magnesium secondary battery according to the present invention, a bipolar magnesium cell having a structure similar to an actual battery was produced as shown in FIG. 3. The assembly was performed in an argon gas atmosphere with a moisture concentration of 0.5 ppm or less and an oxygen concentration of 0.5 ppm or less. For the negative electrode, magnesium metal that was polished in an argon gas atmosphere was used. For the positive electrode, a $V_2O_5$-mixed positive electrode material was used. The $V_2O_5$-mixed positive electrode material was produced using $V_2O_5$ as an active material, polyimide as a binding agent, vapor-grown carbon fiber and Ketjen black as conductive auxiliary agents, and aluminium metal as a collector. A glass fiber sheet was used as a separator.

Charge-and-Discharge Test

Examples 3 to 9 and Comparative Examples 1 to 3 below show the results of charge-and-discharge test for battery cells obtained by combining various electrolyte solutions with the above Mg-metal negative electrode, $V_2O_5$-mixed positive electrode material, and glass separator.

Comparative Example 1

Figure 4:
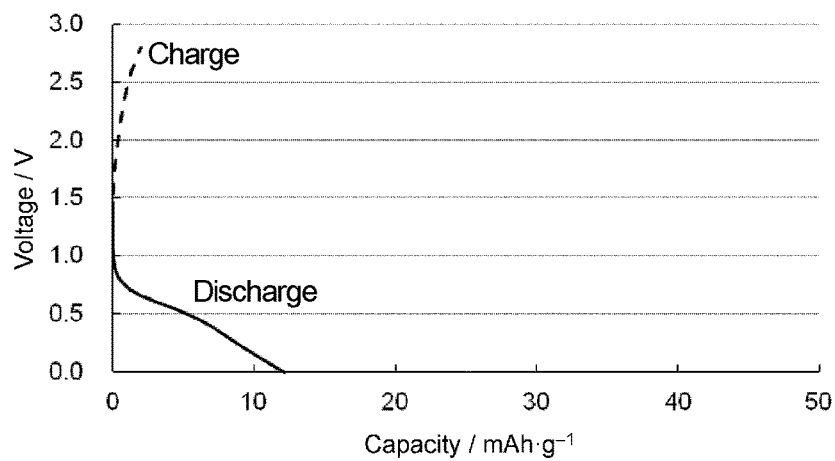
FIG. 4: Initial charge and discharge with the use of an acetonitrile electrolyte solution. A charge-and-discharge test was performed at 25° C. by allowing a separator to be impregnated with an electrolyte solution obtained by dissolving $Mg[Tf_2N]_2$ in acetonitrile at a molar concentration of 0.5 mol·dm$^3$, and combining a magnesium metal negative electrode and a vanadium pentoxide-mixed positive electrode material. The charge-and-discharge rate was equivalent to 0.05 C (10 µA·cm$^{-2}$), on condition that magnesium ions were inserted in/extracted from $V_2O_5$ at a molar ratio of 1:1.

An electrolyte solution obtained by dissolving $Mg[Tf_2N]_2$ in acetonitrile at a molar concentration of 0.5 mol·dm$^{-3}$ was used to construct a battery cell, and a charge-and-discharge test was performed at 25° C. FIG. 4 shows the results. The charge-and-discharge rate was 10 μA·cm$^{-2}$. This electric current value is equivalent to 0.05 C, on condition that magnesium ions are inserted in/extracted from $V_2O_5$ at a molar ratio of 1:1. For cutoff voltage, the lower limit was 0 V, while the upper limit was 2.8 V. Although the theoretical capacity of $MgV_2O_5$ is 294 mAh·g$^{-1}$, the overvoltage was high at the initial discharge, and the voltage reached the lower cutoff limit at a discharge capacity of 12 mAh·g$^{-1}$. When the mode was switched to charge, the overvoltage became even higher, and the voltage reached the upper cutoff limit at a charge capacity of 2 mAh·g$^{-1}$. Thus, reversible charge-discharge cycling did not occur.

Comparative Example 2

Figure 5:
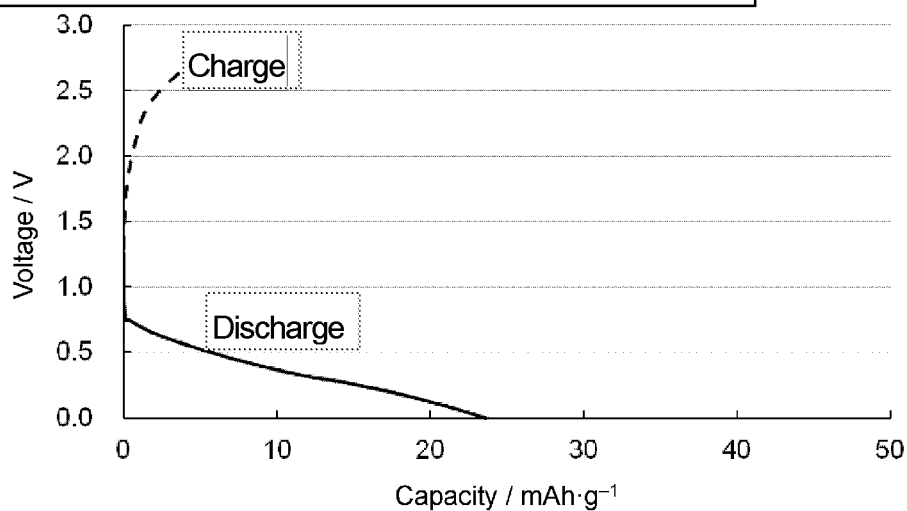
FIG. 5: Initial charge and discharge with the use of a triglyme electrolyte solution. A charge-and-discharge test was performed at 80° C. using an electrolyte solution obtained by dissolving $Mg[Tf_2N]_2$ in triglyme at a molar ratio of 1:5, and combining the same electrode and separator as in FIG. 4.

A battery cell was constructed using an electrolyte solution obtained by dissolving $Mg[Tf_2N]_2$ in triglyme at a molar ratio of 1:5, and a charge-and-discharge test was performed at 80° C. FIG. 5 shows the results. The charge-and-discharge rate and cutoff voltage were respectively 10 μA·cm$^{-2}$ and 0 to 2.8 V, as in Comparative Example 1. The discharge capacity with the use of this electrolyte solution was 23 mAh·g$^{-1}$, which was slightly improved, compared with Comparative Example 1. This is because the use of a solvent having a boiling point higher than the boiling point of acetonitrile achieved an increase in the operating temperature, thereby reducing the overvoltage. When the mode was switched to charge, the voltage reached the upper cutoff limit at a charge capacity of 6 mAh·g$^{-1}$, and reversible charge-discharge cycling did not occur.

Comparative Example 3

Figure 6:
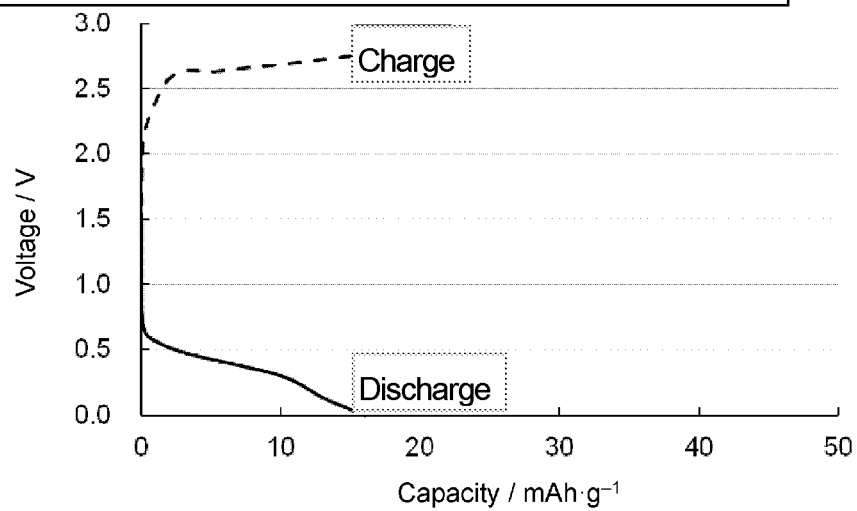
FIG. 6: Initial charge and discharge with the use of a sulfolane electrolyte solution. A charge-and-discharge test was performed at 80° C. using an electrolyte solution obtained by dissolving $Mg[Tf_2N]_2$ in sulfolane at a molar concentration of 0.5 mol·dm$^3$, and combining the same electrode and separator as in FIG. 4.

A battery cell was constructed using an electrolyte solution obtained by dissolving $Mg[Tf_2N]_2$ in sulfolane at a molar concentration of 0.5 mol·dm$^{-3}$, and a charge-and-discharge test was performed at 80° C. FIG. 6 shows the results. The charge-and-discharge rate and cutoff voltage were respectively 10 μA·cm$^{-2}$ and 0 to 2.8 V, as in Examples 4 to 5. The discharge capacity with the use of this electrolyte solution was 16 mAh·g$^{-1}$. Then, when the mode was switched to charge, charge was performed to the same value within the cutoff voltage range.

Example 3

Figure 7:
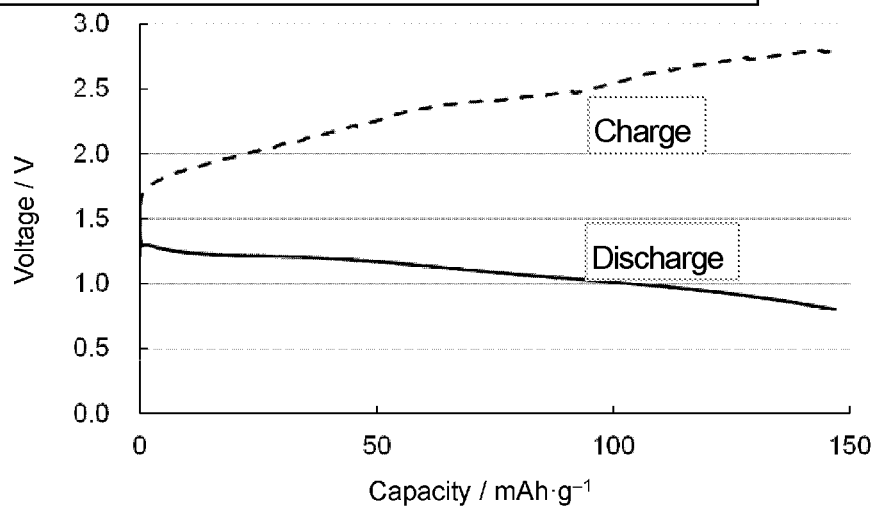
FIG. 7: Initial charge and discharge with the use of a $[N_{2,2,2,2}]$ $[Tf_2N]$ electrolyte solution. A charge-and-discharge test was performed at 150° C. using an electrolyte solution obtained by dissolving $Mg[Tf_2N]_2$ in $[N_{2,2,2,2}]$ $[Tf_2N]$ at a molar ratio of 1:9, and combining the same electrode and separator as in FIG. 4.

A battery cell was constructed using an electrolyte solution obtained by dissolving $Mg[Tf_2N]_2$ in $[N_{2,2,2,2}]$ $[Tf_2N]$ at a molar ratio of 1:9, and a charge-and-discharge test was performed at 150° C. FIG. 7 shows the results. The charge-and-discharge rate and cutoff voltage were respectively 10 μA·cm$^{-2}$ and 0 to 2.8 V, as in Comparative Examples 1 to 3. Unlike Comparative Examples 1 to 3, the voltage did not reach the lower cutoff limit at the initial discharge until the discharge capacity reached 146 mAh·g$^{-1}$. When the mode was switched to charge, charge was performed to the same capacity within the cutoff voltage range. This value is much greater than those of Comparative Examples 1 to 3, which indicates that an ionic liquid electrolyte solution that enables high-temperature operation is capable of high-capacity, reversible charge and discharge.

Example 4

Figure 8:
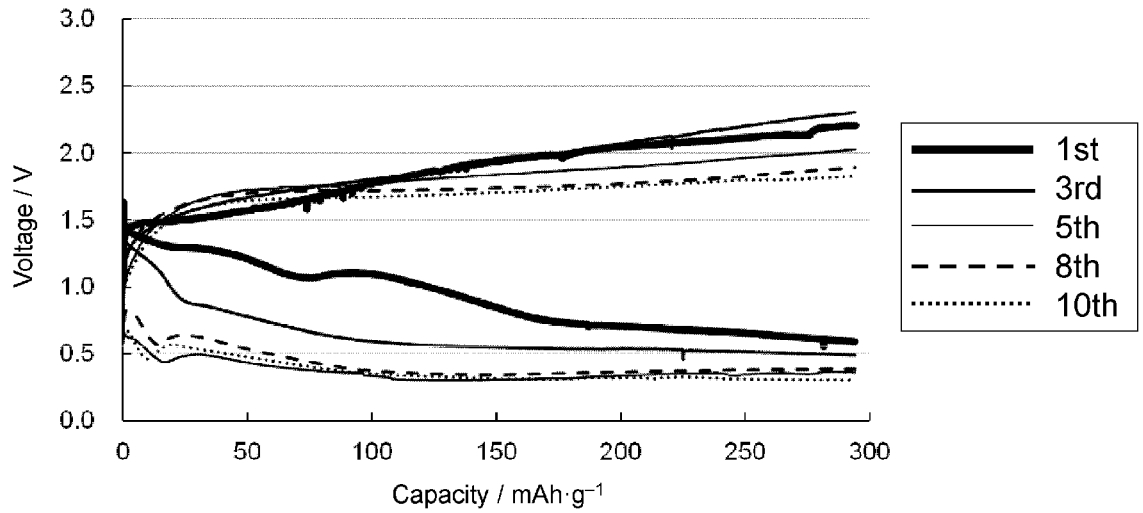
FIG. 8: Charge-and-discharge cycle with the use of a $[N_{2,2,2,2}]$ $[Tf_2N]$ electrolyte solution. A test cell was separately produced using the same electrolyte solution as in FIG. 7, and discharge and charge were repeated at a temperature of 200° C. and a charge-and-discharge rate equivalent to 0.1 C (20 µA·cm$^2$).

The same battery cell as in Example 3 was separately produced, and a charge-and-discharge test was performed at 200° C. FIG. 8 shows the results. The charge-and-discharge rate was 20 μA·cm$^{-2}$, which is twice as much as in Comparative Examples 1 to 3 or Example 3. The cutoff voltage was 0 to 2.8 V, as in Comparative Examples 1 to 3 or Example 3. This electric current value is equivalent to 0.1 C, on condition that magnesium ions are inserted in/extracted from $V_2O_5$ at a molar ratio of 1:1. At the initial discharge, the discharge capacity reached 294 mAh·g$^{-1}$, which is equal to the theoretical capacity of $MgV_2O_5$. Then, when the mode was switched to charge, the same capacity was charged within a clamping voltage range. Thereafter, when charge and discharge were repeated under the same conditions, the theoretical capacity was obtained during 10 charge/discharge cycles, as in the first cycle.

Example 5

Figure 9:
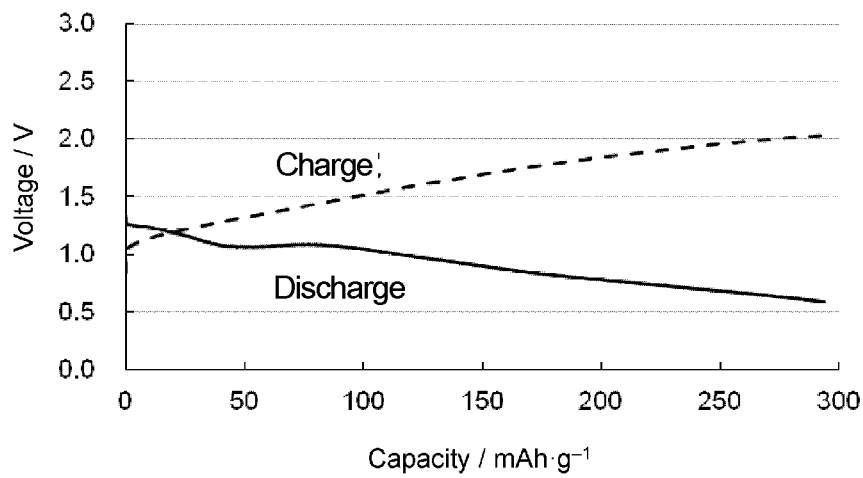
FIG. 9: Initial charge and discharge with the use of a [EMI] $[Tf_2N]$ electrolyte solution. A charge-and-discharge test was performed using an electrolyte solution obtained by dissolving $Mg[Tf_2N]_2$ in [EMI] $[Tf_2N]$ at 0.5 mol·dm$^3$, and combining the same electrode and separator as in FIG. 7.

A battery cell was constructed using an electrolyte solution obtained by dissolving $Mg[Tf_2N]_2$ in [EMI] $[Tf_2N]$ at 0.5 mol·dm$^3$, and a charge-and-discharge test was performed at 200° C. FIG. 9 shows the results. The charge-and-discharge rate and cutoff voltage were respectively 20 μA·cm$^{-2}$ and 0 to 2.8 V, as in Example 4. The discharge capacity reached 294 mAh·g$^{-1}$, which is equal to the theoretical capacity of $MgV_2O_5$, and when the mode was switched to charge, charge was performed to the same capacity within the cutoff voltage range, as in Example 4.

Example 6

Figure 10:
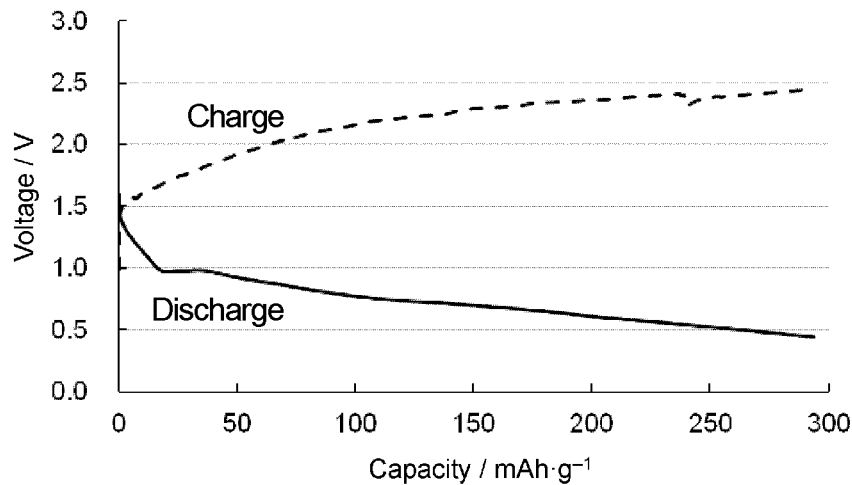
FIG. 10: Initial charge and discharge with the use of a $[AS_{44}]$ $[Tf_2N]$ electrolyte solution. A charge-and-discharge test was performed using an electrolyte solution obtained by dissolving $Mg[Tf_2N]_2$ in $[AS_{44}]$ $[Tf_2N]$ at a molar ratio of 1:9, and combining the same electrode and separator as in FIG. 7.

A battery cell was constructed using an electrolyte solution obtained by dissolving $Mg[Tf_2N]_2$ in $[PS_{44}][Tf_2N]$ at a molar ratio of 1:9, and a charge-and-discharge test was performed at 200° C. FIG. 10 shows the results. The charge-and-discharge rate and cutoff voltage were respectively 20 μA·cm$^{-2}$ and 0 to 2.8 V, as in Examples 4 to 5. The discharge capacity reached 294 mAh·g$^{-1}$, which is equal to the theoretical capacity of MgV$_2$O$_5$, and when the mode was switched to charge, charge was performed to the same capacity within the cutoff voltage range, as in Examples 4 to 5.

Example 7

Figure 11:
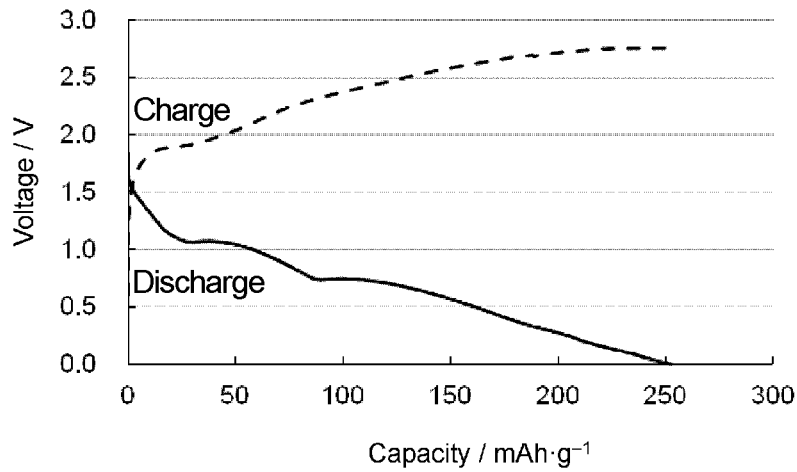
FIG. 11: Initial charge and discharge with the use of a $[P_{2,2,2,2}]$ $[Tf_2N]$ electrolyte solution. A charge-and-discharge test was performed using an electrolyte solution obtained by dissolving $Mg[Tf_2N]_2$ in $[P_{2,2,2,2}]$ $[Tf_2N]$ at a molar ratio of 1:9, and combining the same electrode and separator as in FIG. 7.

A battery cell was constructed using an electrolyte solution obtained by dissolving Mg[Tf$_2$N]$_2$ in [P$_{2,2,2,2}$] [Tf$_2$N] at a molar ratio 1:9, and a charge-and-discharge test was performed at 200° C. FIG. 11 shows the results. The charge-and-discharge rate and cutoff voltage were respectively 20 μA·cm$^{-2}$ and 0 to 2.8 V, as in Examples 4 to 6. The voltage reached the lower cutoff limit at a discharge capacity of 250 mAh·g$^{-1}$. When the mode was switched to charge, charge was performed to the same capacity within the cutoff voltage range.

Example 8

Figure 12:
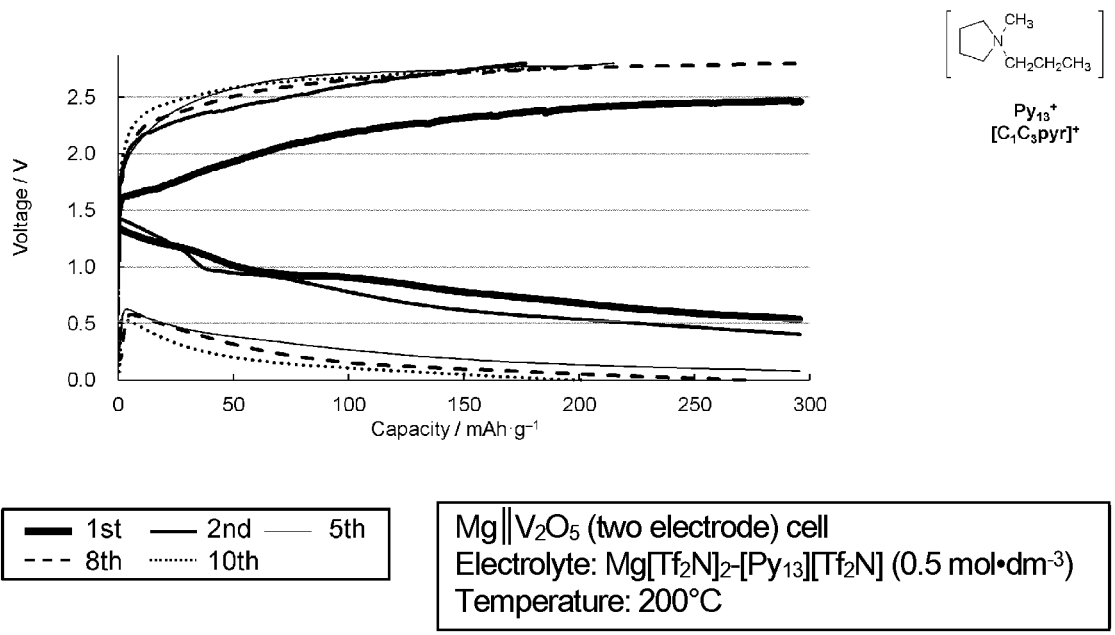
FIG. 12: Impedance measurement of a $[N_{2,2,2,2}]$ $[Tf_2N]$ electrolyte solution. A bipolar symmetrical cell of magnesium metal was produced using an electrolyte solution obtained by dissolving $Mg[Tf_2N]_2$ in $[N_{2,2,2,2}]$ $[Tf_2N]$ at a molar ratio of 1:9, and the temperature dependency of interfacial charge-transfer resistance with respect to the magnesium metal was measured, based on the electrochemical AC impedance measurement.

A battery cell was constructed using an electrolyte solution obtained by dissolving Mg[Tf$_2$N]$_2$ in [Py$_{13}$][Tf$_2$N] at 0.5 mol·dm$^{-3}$, and a charge-and-discharge test was performed at 200° C. FIG. 12 shows the results. The charge-and-discharge rate and cutoff voltage were respectively 20 μA·cm$^{-2}$ and 0 to 2.8 V, as in Example 4. The discharge capacity reached 294 mAh·g$^{-1}$, which is equal to the theoretical capacity of MgV$_2$O$_5$, and when the mode was switched to charge, charge was performed to the same capacity within the cutoff voltage range, as in Example 4.

Example 9

Figure 13:
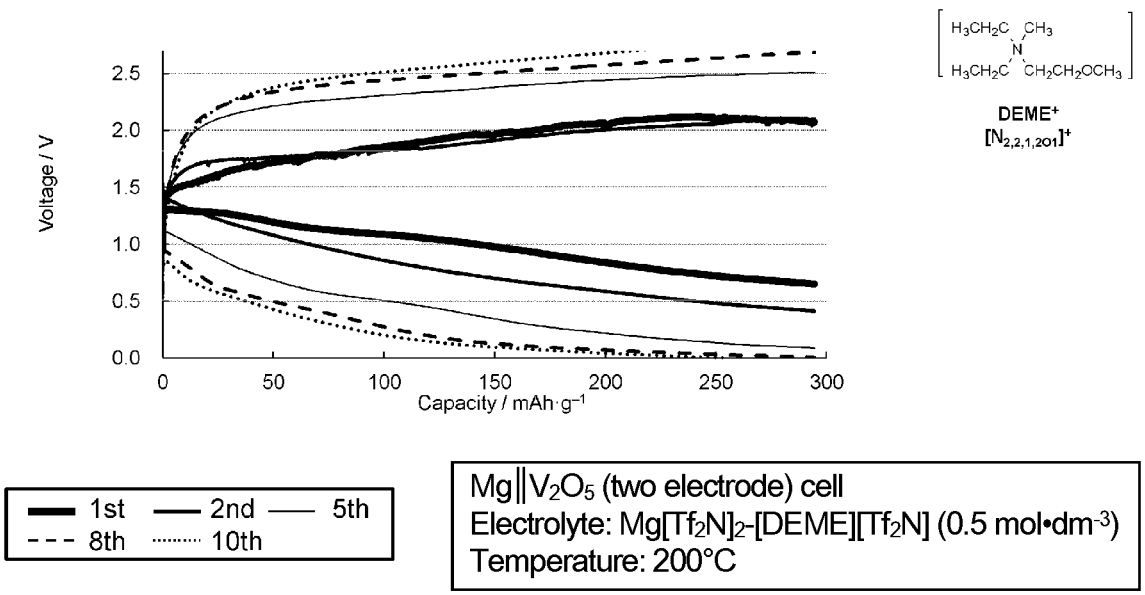
FIG. 13: Overvoltage measurement of a $[N_{2,2,2,2}]$ $[Tf_2N]$ electrolyte solution. The overvoltage was measured using the same test cell as in FIG. 10, and applying a constant current for a short time (10 µA for 10 minutes).

A battery cell was constructed using an electrolyte solution obtained by dissolving Mg[Tf$_2$N]$_2$ in [DEME][Tf$_2$N] at 0.5 mol·dm$^{-3}$, and a charge-and-discharge test was performed at 200° C. FIG. 13 shows the results. The charge-and-discharge rate and cutoff voltage were respectively 20 μA·cm$^{-2}$ and 0 to 2.8 V, as in Example 4. The discharge capacity reached 294 mAh·g$^{-1}$, which is equal to the theoretical capacity of MgV$_2$O$_5$, and when the mode was switched to charge, charge was performed to the same capacity within the cutoff voltage range, as in Example 4.

Example 10

Figure 14:
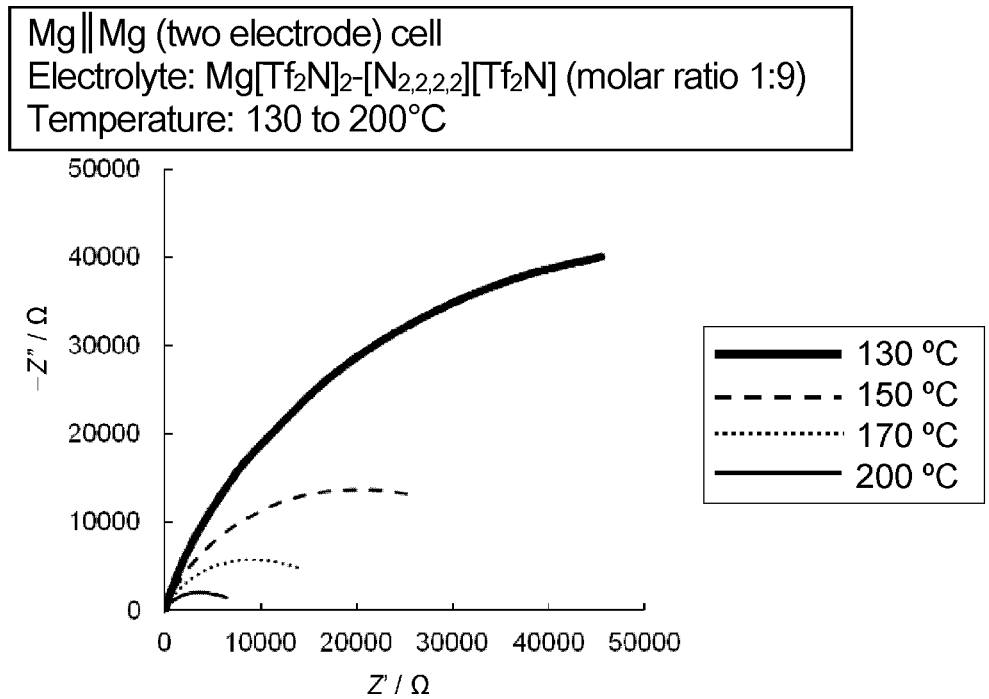
FIG. 14: The charge-and-discharge cycle of a $[Py_{13}]$ $[Tf_2N]$ electrolyte solution.

A bipolar symmetrical cell was produced in which an electrolyte solution obtained by dissolving Mg[Tf$_2$N]$_2$ in [N$_{2,2,2,2}$] [Tf$_2$N] at a molar ratio of 1:9 was sandwiched between two magnesium metal materials, and an electrochemical AC impedance measurement was performed. FIG. 14 shows the results. The width of the circular arcs in the figure represents the interfacial charge-transfer resistance of the electrolyte solution with respect to the magnesium metal. Such resistance was confirmed to greatly decrease as the temperature increases.

Example 11

Figure 15:
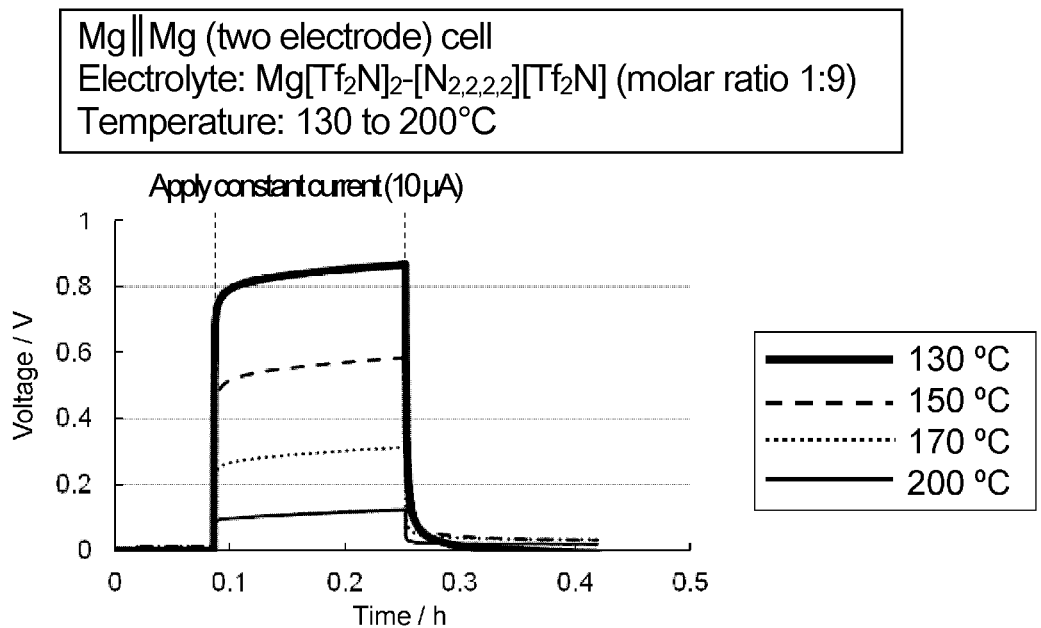
FIG. 15: The charge-and-discharge cycle of a [DEME] $[Tf_2N]$ electrolyte solution.

An electric current of 10 μA was applied for 10 minutes using the same magnesium symmetrical cell as in Example 10, and the overvoltage was measured. FIG. 15 shows the results. An increase in the temperature greatly reduced the overvoltage, which is consistent with the decrease in the interfacial charge-transfer resistance as confirmed in Example 10.

Example 12

Figure 16:
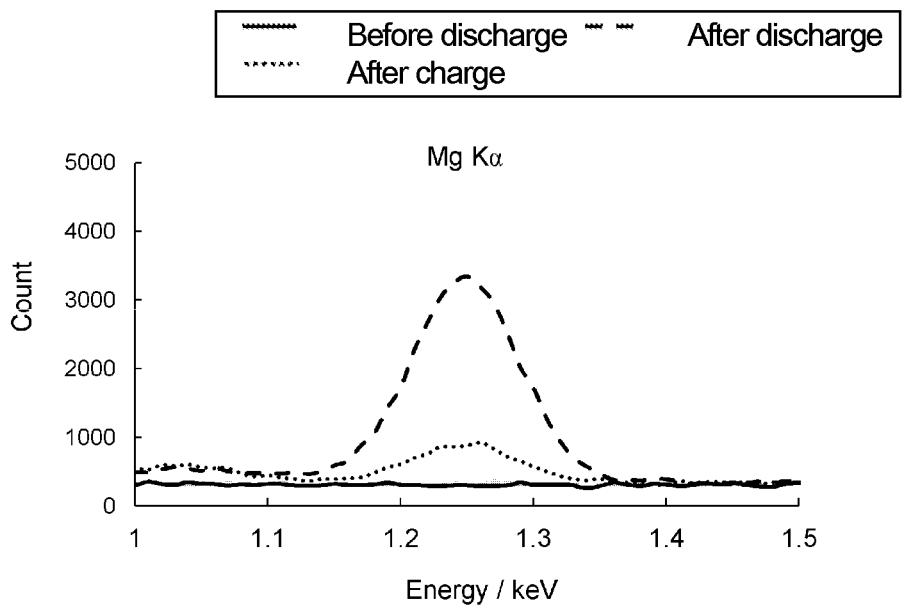
FIG. 16: X-ray fluorescence analysis of $V_2O_5$ positive electrode.

Three battery cells were produced comprising a combination of an electrolyte solution obtained by dissolving Mg[TfiN]$_2$ in [N$_{2,2,2,2}$] [Tf$_2$N] at a molar ratio of 1:9, an Mg-metal negative electrode, and a V$_2$O$_5$ positive electrode that uses a stainless-steel collector. The V$_2$O$_5$ positive electrodes were collected from the batteries in each state (i.e., one that was before discharge (no charge and discharge were performed), one that was discharged at 200° C., and one that was discharged and charged at 200° C.), and X-ray fluorescence analysis was performed for these V$_2$O$_5$ positive electrodes. FIG. 16 shows the results. Although no peak corresponding to Mg Kα was observed before discharge, the peak was observed after discharge, which indicates that Mg ions were inserted into the V$_2$O$_5$ positive electrode as a result of discharge. The Mg peaks of the V$_2$O$_5$ positive electrodes before discharge and after charge were greatly reduced, compared to that only being discharged, which indicates that Mg ions were extracted from the V$_2$O$_5$ positive electrode as a result of charge. The results of FIG. 16 confirm that the V$_2$O$_5$ used as a positive electrode active material is a material in which magnesium ions undergo an insertion/extraction reaction.

The invention claimed is:

1. A non-aqueous electrolyte magnesium secondary battery comprising a positive electrode, a negative electrode, a separator, and a non-aqueous electrolyte,
   wherein the non-aqueous electrolyte consists of Mg[N(SO$_2$CF$_3$)$_2$]$_2$ as an electrolyte salt and an ionic liquid as a solvent,
   wherein the ionic liquid consists of [N(SO$_2$CF$_3$)$_2$]$^-$ as an anion and an organic onium cation as a cation,
   wherein the organic onium cation is at least one cation selected from the group consisting of tetramethylammonium (N$_{1111}$), tetraethylammonium (N$_{2222}$), tetra n-propylammonium (N$_{3333}$), tetra n-butylammonium (N$_{4444}$), tetra n-pentylammonium (N$_{5555}$), and 5-azoniaspiro[4.4]nonane (AS$_{44}$).

2. The non-aqueous electrolyte magnesium secondary battery according to claim 1, wherein the negative electrode comprises a negative electrode active material selected from the group consisting of a metal magnesium, a magnesium alloy material, a carbon material, a composite material of metal magnesium, and a composite material of a magnesium alloy with a carbon material.

3. The non-aqueous electrolyte magnesium secondary battery according to claim 1, wherein the positive electrode comprises a positive active material, and the positive active material is a material in which magnesium ions undergo an insertion/extraction reaction.

4. The non-aqueous electrolyte magnesium secondary battery according to claim 3, wherein the material in which magnesium ions undergo an insertion/extraction reaction is at least one material selected from the group consisting of a metal sulfide free from magnesium, a metal oxide free from magnesium, an oxide obtained by removing Li from a Li-containing composite oxide and replacing the Li with an Mg ion, a Chevrel material, a polyanion material, a silicate material, a magnesium nitride, an organic positive-electrode material, a compound containing a transition metal and fluorine, and a halogenated compound.

5. The non-aqueous electrolyte magnesium secondary battery according to claim 3, wherein the material in which magnesium ions undergo an insertion/extraction reaction is at least one material selected from the group consisting of $TiS_2$, $MoS_2$, $NbSe2$, $CoS$, $V_2O_5$, $V_8O_{13}$, $MnO_2$, $CoO_2$, $MgMn_2O_4$, $MgAlO_3$, $MgMnO_3$, $MgFeO_3MgFe_{0.5}Mn_{0.5}O_3$, $MgFe_{0.9}Al_{0.1}O_3$, $MgMn_{0.9}Al_{0.1}O_3$, $Mg_{0.5}Mn_{0.9}Al_{0.1}O_2$, $Mo_6S_8$, $MxMo_6S_8$ (M=Cu, Ni, Ag, a transition metal, 0≤x≤2), $Cu_{0.13}Mg_{1.09-1.12}Mo_6S_8$, $MgHf(MoO_4)_3$, $Mg_{0.5}Hf_{0.5}Sc_{1.0}(MoO_4)_3$, $Mg_{0.2}Zr_{0.2}Sc_{1.6}(WO_4)_3$, $Mg_{0.4}Zr_{0.4}Sc_{1.2}(WO_4)_3$, $Mg_{0.6}Zr_{0.6}Sc_{1.2}(WO_4{}_3$, $Mg_{0.8}Zr_{0.8}Sc_{0.4}(WO_4)_3$, $MgZr(WO_4)_3$, $MgCoSiO_4$, $MgFeSiO_4$, $MgNiSiO_4$, $Mg(Ni_{0.9}Mn_{0.1})SiO_4$, $MgFe_{0.9}Si_{0.1}O_3$, $MgFe_{0.5}Si_{0.5}O_3$, $MgFe_{0.1}Si_{0.9}O_3$, $Mg_{1.023}(Mn_{0.956}V_{0.014})SiO_4$, $FeF_{2.8}Cl_{0.2}MgCOSiO_4$, $MgMn_{0.9}Si_{0.1}O_3$, $Mg_{0.9925}(Co_{0.985}V_{0.015})SiO_4$, $Mg_{0.959}(Fe_{0.918}V_{0.082})SiO_4$, $Mg_{0.95}(Ni_{0.9}V_{0.100})SiO_4$, magnesium nitride, magnesium porphyrin, a polythiophene, $FeF_3$, and $MnF_3$.

6. The non-aqueous electrolyte magnesium secondary battery according to claim 1, wherein the organic onium cation is tetraethylammonium ($N_{2222}$) or 5-azoniaspiro[4.4]nonane ($AS_{44}$).

\* \* \* \* \*